(12) United States Patent
Narayanan et al.

(10) Patent No.: US 6,251,416 B1
(45) Date of Patent: Jun. 26, 2001

(54) WATER-BASED MICROEMULSION OF A PYRETHROID

(75) Inventors: Kolazi S. Narayanan, Wayne, NJ (US); Domingo Jon, New York, NY (US); Robert M. Ianniello, Oak Ridge; Donald Prettypaul, Englewood, both of NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 09/542,350

(22) Filed: Apr. 4, 2000

Related U.S. Application Data

(62) Division of application No. 09/098,658, filed on Jun. 17, 1998, now Pat. No. 6,045,816.

(51) Int. Cl.$^7$ ..................................................... A01N 25/02

(52) U.S. Cl. ..................... 424/405; 424/406; 424/78.17; 424/78.18; 424/78.31; 514/772.1; 514/772.4; 514/772.7; 514/784; 514/785; 514/937; 514/941; 514/943

(58) Field of Search ..................................... 424/405, 406, 424/78.17, 78.18, 78.31; 514/66, 531, 572, 937, 941, 943, 772.1, 772.4, 772.7, 938, 970, 971, 784, 785, 772.6

(56) References Cited

U.S. PATENT DOCUMENTS 5,427,794 * 6/1995 Miles ................................... 424/405

* cited by examiner

*Primary Examiner*—Neil S. Levy
(74) *Attorney, Agent, or Firm*—Walter Katz; William J. Davis; Marilyn J. Maue

(57) ABSTRACT

A clear, one-phase, efficacious aqueous microemulsion of an agriculturally active pyrethroid insecticide for delivery at a high loading of active is provided herein which is free of nonylphenol ethoxylate.

1 Claim, No Drawings

WATER-BASED MICROEMULSION OF A PYRETHROID

This application is a Divisional of Ser. No. 09/098658, filed Jun. 17, 1998, now U.S. Pat. No. 6,045,816.

BACKGROUND OF THE INVENTION

1. Field of the Invention

This invention relates to a delivery system for agriculturally active chemicals, and, more particularly, to a clear, one-phase, efficacious aqueous microemulsion for delivering a pyrethroid insecticide at a high loading.

2. Description of the Prior Art

Agriculturally active chemicals are most preferably applied in the form of aqueous emulsions, solutions or suspensions. Occasionally, they may also be applied in the form of a dust wherein the active ingredient is adsorbed onto or mixed with a finely divided inert carrier material, such as, china clay, or the like. With such powdered or dust compositions, drift due to wind is a problem and consequently, liquid formulations are preferred.

One of the problems with such liquid formulations is the fact that chemicals having agricultural activity often exhibit extreme insolubility in water. This results in their having to be dissolved either in organic solvents or utilized in the form of emulsions or suspensions. With respect to the use of organic solvents, these are generally disadvantageous from an environmental and cost viewpoint. Particularly, such organic chemicals may exhibit toxicity or side-effects which may be adverse to the effect of the agricultural chemical itself or to the subsequent fruit or vegetable produced in the particular agricultural use. This toxicity may also be disadvantageous with respect to handling.

When attempts are made to provide emulsified or suspension formulations, difficulties are encountered with respect to providing a desirably high concentration of the agriculturally active ingredient. Thus, when such agriculturally active chemicals are formulated into a macroemulsion (sometimes referred to herein as an emulsion), it is difficult to maintain the emulsified state. This, in turn, creates problems in maintaining a uniform formulation, particularly, when the formulation is diluted with water for application to the plants.

U.S. Pat. No. 5,317,042 disclosed a clear stable, efficacious aqueous microemulsion of a pyrethroid insecticide, alone, or in a complex mixture, obtained by mixing the insecticide with an inert matrix composition containing a defined mixture of nonionic surfactant to form a microemulsion concentrate, and diluting with water. The inert matrix composition consisted of a predetermined mixture of non-ionic surfactants which also included nonylphenol ethoxylate with HLB>6. However, the presence of nonylphenol ethoxylate in the formulation may be considered detrimental in some cases.

It is also desired to provide an aqueous microemulsion a pyrethroid insecticide which is free of nonylphenol ethoxylate, and which is stable upon formation, and which can be used within a relatively long time, without significant hydrolysis or precipitation.

SUMMARY OF THE INVENTION

What is provided herein is a clear, one-phase, efficacious aqueous microemulsion of an agriculturally active pyrethroid insecticide, which is free of nonylphenol ethoxylate, and which comprises, by weight:

(a) about 0.0005–5%, preferably 0.01–3% of said pyrethroid, (b) about 0–6%, preferably 0.015–4%, of N- $C_1$–$C_4$ alkyl pyrrolidone, preferably N-methyl pyrrolidone, (c) about 0.0002–4%, preferably 0.005–2%, of a $C_6$–$C_{18}$ a alkyl pyrrolidone, preferably N-octyl pyrrolidone, (d) 0–3%, preferably 0.05–1.5%, of an EO/PO block copolymer surfactant, (e) 0.003–10%, preferably 0.04–6%, of an ethoxylated castor oil or a tristyryl phenol ethoxylate, and (f) 0–1%, preferably 0.0005–0.6% of a phosphate ester as a pH buffer, (g) at least about 80% of water, preferably 90–99.99%.

DETAILED DESCRIPTION OF THE INVENTION

Surfactant Trade Names

Pluronic® L31-EO/PO block copolymer surfactants, BASF
Igepal® CO-630-Nonylphenol ethoxylate, Rhone-Poulenc
Soprophor® BSU-Tristyrylphenol ethoxylate, Rhone-Poulenc
Soprophor® 3D-33-Tristyrylphenol ethoxylate phosphate ester, Rhone-Poulenc
Alkamuls® EL 620-Ethoxylated Castor Oil, Rhone-Poulenc
Gafac® RE-610-Nonylphenol ethoxylate phosphate ester, Rhone-Poulenc
Rhodafac® RA 600-Linear ethoxylate phosphate ester, Rhone-Poulenc
Rhodafac® RS 710-Branched ethoxylate phosphate ester, 9.75 E.O., Rhone-Poulenc A pyrethroid is a class of well known and widely-used insecticides of which cypermethrin, o-allethrin, permethrin, piperonyl butoxide and tetramethrin are representative examples. In accordance with the invention a clear, efficacious, aqueous, microemulsion of a pyrethroid was formulated having the following components, in parts by weight.

TABLE 1

AQUEOUS MICROEMULSION COMPOSITION OF THE INVENTION

| | | Amounts (% by Wt.) | |
|---|---|---|---|
| | Component | Suitable | Preferred |
| (a) | Pyrethroid e.g. cypermethrin | 0.0005–4 | 0.010–3 |
| (b) | $C_1$–$C_4$ alkyl pyrrolidone e.g. N-methyl pyrrolidone | 0–6 | 0.015–4 |
| (c) | $C_6$–$C_{18}$ alkyl pyrrolidone, e.g. octyl pyrrolidone | 0.0002–4 | 0.005–2 |
| (d) | EO/PO block copolymer e.g. Pluronic ® L31 | 0–3 | 0.05–1.5 |
| (e) | Ethoxylate of Castor Oil or tristyryl phenol ethoxylate, e.g. Alkamuls ® EL-620 or Soprophor ® BSU | 0.003–10 | 0.04–6 |
| (f) | Phosphate ester, e.g. Soprophor ® 3D-33, Rhodafac ® RS 710 or Rhodafac ® RA 600 | 0–1% | 0.005–0.6% |
| (8) | Water | >80 | 90–99.99 |
| | | 100.0 | 100.0 |

This composition is a stable, one-phase, efficacious microemulsion of pH<4 at ambient temperatures free of nonylphenol ethoxylate and which is designed for use after preparation.

Other agricultural active chemicals which may be included in the compositions of the invention are: permethrin; permethrin+Kathon®, D-allethrin; tetramethrin; deltamethrin; piperonyl butoxide; mixed pyrethroids; dicofol; tefluthrin; resmethrin; phenothrin; kadethrin; bifenthrin; cyhalothrin; cycloprothrin; tralomethrin; cyfluthrin; fenvalerate and isomers; fenpropathrin; fluvalenate; rotenone; biphenyl compounds like, methoxychlor; chlorbenzilate; bromopropylate and chlorfenethol.

The following are specific examples of the invention.

TABLE 2

| COMPOSITION | | | |
|---|---|---|---|
| | 2A | 2B | 2C |
| Microemulsion Concentrate (MEC) | | | |
| N-Methyl pyrrolidone | 0.89 | 1.33 | 1.78 |
| N-Octyl pyrrolidone | 0.39 | 0.58 | 0.78 |
| Pluronic ® L31 | 0.39 | 0.58 | 0.78 |
| Alkamuls ® EL-620 or Soprophor ® BSU | 2.34 | 3.50 | 4.67 |
| Active Pyrethroid | | | |
| D-Allethrin | 0.05 | 0.05 | 0.05 |
| Permethrin | 0.15 | 0.15 | 0.15 |
| Tetramethrin | 0.2 | 0.2 | 0.2 |
| Piperonyl Butoxide | 1.0 | 1.0 | 1.0 |
| Microemulsion/Dilution Water | | | |
| 1000 ppm hard water | 94.6 | 92.6 | 92.6 |
| Total Concentration | 100.0 | 100.0 | 100.0 |
| Properties of MEC at RT at | Appearance | | |
| 0 hr. | clear | clear | clear |
| 24 hr. | clear | clear | clear |
| 2 days | clear | clear | clear |
| 2 weeks | clear | clear | clear |

The compositions of the invention could be stored at <−5° C. without freezing or separating the active.

Experimental Procedure

A. Formulations

An Inert Matrix Composition is provided for forming a stable, clear efficacious Microemulsion Concentrate (MEC). Upon dilution of the concentrate with water, an aqueous microemulsion is provided. The Inert Matrix Composition was prepared by mixing predetermined amount of $C_8$ alkylpyrrolidone, defined nonionic surfactants, and preferably with $C_1$ alkylpyrrolidone. The Agricultural Active Chemical (AAC) was added and the mixture shaken until the dissolution of AAC or the mixture became homogeneous. Normally this took about thirty minutes to two hours. A MEC was obtained which was either diluted immediately at ratios 1:10, 1:100, 1:1000 and 1:10,000 or stored.

The water based microemulsion were prepared by adding the required quantity of the concentrate to water. The dilution water was either deionized water or World Health Organization (WHO) standard hard water of hardness of 1000 ppm expressed as $CaCO_3$ equivalent.

B. Evaluation of Stability

The concentrate and diluted samples were visually examined for clarity, precipitation, separation and turbidity at ambient temperature. Stable formulations were observed as long as six months. The formulations were considered stable if they remained clear by visual observation for more than 4 days. Formulations that became cloudy or separated within 24 hours were considered unstable.

The aqueous microemulsion composition of the invention made according to the above procedure are summarized from TABLE 1 to TABLE 4 below, wherein the components are in grams. The stability of the microemulsion after standing at room temperature for a considerable period are also included.

EXAMPLE 1

A series of microemulsion and miniemulsion concentrates were prepared using various amounts of cypermethrin. An inert matrix M1 was prepared first by mixing 21.3 g of N-methylpyrrolidone, 9.3 g N-octyl-pyrrolidone, 9.3 g of Pluronic L31, 56.0 g of Soprophor BSU and 4.0 g of Soprophor 3D-33. Microemulsion concentrates were prepared by mixing 10 g, 15 g, 20 g and 25 g cypermethrin with 90 g, 85 g, 80 g, and 75 g of matrix M1, respectively, as seen in Table 3. The above microemulsion concentrate were diluted at ratios 1:10, 1:100 and 1:1000 with 1000 ppm hard water. All the diluted samples were clear except at 1:10 and 1:100 aqueous dilutions of 20% and 25% cypermethrin. At these dilutions, miniemulsions were obtained that were stable for at least a day. The particle size at 1:10 dilution of 10% and 15% cypermethrin were less than 0.013 and 0.014 microns at 90% population, respectively. Freeze/thaw stability studies between 5 and −10° C. were carried out with the concentrate containing 15% cypermethrin. The results showed a stable, liquid formulation at the lowest temperature described.

HPLC analysis of the concentrate containing 25% cypermethrin showed greater than 99% retention of a.i. after storing the sample at 52° C. for 18 days.

TABLE 3

| Composition | 1 | 2 | 3 | 4 |
|---|---|---|---|---|
| Microemulsion Concentrate | | | | |
| Inert Matrix M1 | 90 | 85 | 80 | 75 |
| Cypermethrin | 10 | 15 | 20 | 25 |
| Water-Based Microemulsion | | | | |
| Properties of Aqueous Microemulsion at 19° C. dilution ratio with 1000 ppm hard water | | | | |
| 1:10 | clear | clear | cloudy | cloudy |
| 1:100 | clear | clear | haze | haze |
| 1:1000 | clear | clear | clear | clear |

EXAMPLE 2

The role of N-methylpyrrolidone in the microemulsion of Example 1 was investigated. An inert matrix M2 was prepared first by mixing 10 g N-octylpyrrolidone, 10 g of Pluronic L31, 60 g of Soprophor BSU and 4.3 g of Soprophor 3D-33. A concentrate was prepared by mixing 15 g of cypermethrin with 85 g of the matrix M2. The microemulsion concentrate was diluted at ratios 1:10, 1:100 and 1:1000 with 1000 ppm hard water. All the diluted samples were clear. Freeze/thaw stability study between 5 and −10° C. carried out with the concentrate showed a stable, thick paste at −5° C. and lower temperatures.

EXAMPLE 3

The role of N-octylpyrrolidone in the microemulsion of Example 1 was investigated. An inert matrix M3 was prepared first by mixing 20 g N-methyl-pyrrolidone, 8.7 g of Pluronic L31, 52.8 g of Soprophor BSU and 3.7 g of Soprophor 3D-33. A concentrate was prepared by mixing 15 g of cypermethrin with 85 g of matrix M3. The microemulsion concentrate was diluted at ratios 1:10, 1:100 and 1:1000 with 1000 ppm hard water. All the diluted samples were stable and clear except at 1:100 dilution, where a precipitate was formed. Freeze/thaw stability study between 5 and −10° C. Carried out with the concentrate showed a stable, thick paste at −5° C. and lower temperatures.

EXAMPLE 4

Similarly, the role of both N-methylpyrrolidone and N-octylpyrrolidone in the microemulsion of Example 1 was investigated. An inert matrix M4 was prepared first by 11.4 g of Pluronic L31, 68.7 g of Soprophor BSU and 4.9 g of Soprophor 3D-33. A concentrate was prepared by mixing 15 g of cypermethrin with 85 g of matrix M4. The microemulsion concentrate was diluted at ratios 1:10, 1:100 and 1:1000 with 1000 ppm hard water. All the diluted samples were stable and clear except at 1:10 dilution, where a precipitate was formed. Freeze/thaw stability study between 5 and −10° C. carried out with the microemulsion concentrate showed a stable, thick paste at −5° C. and lower temperature. Therefore, from the results of Example 1 to Example 4, N-octylpyrrolidone is required to obtain a stable, clear solution with some of the aqueous dilutions in Formulation 2, and both N-methylpyrrolidone and N-octylpyrrolidone are needed to prevent thickening of the samples to a paste at temperature below −5° C.

TABLE 4

| Composition | 1 | 2 | 3 | 4 |
|---|---|---|---|---|
| Microemulsion Concentrate | | | | |
| Inert Matrix M5 | 90 | 85 | 80 | 75 |
| Cypermethrin | 10 | 15 | 20 | 25 |
| Water-Based Microemulsion | | | | |
| Properties of Aqueous Microemulsion at 19° C. dilution ratio with 1000 ppm hard water | | | | |
| 1:10 | clear | haze | haze | haze |
| 1:100 | clear | clear | clear | clear |
| 1:1000 | clear | clear | clear | clear |

EXAMPLE 5

The experiment of Example 1 was repeated after replacing Soprophor BSU in Matrix M1 with equal weight of Alkamuls EL 620 (Matrix M5). Microemulsion concentrates were prepared by mixing 10 g, 15 g, 20 g and 25 g cypermethrin with 90 g, 85 g, 80 g, and 75 g of matrix M5, respectively, as seen in Table 4. The above microemulsion concentrate were diluted at ratios 1:10, 1:100 and 1:1000 with 1000 ppm hard water. All the diluted sample formed clear microemulsions except those samples diluted at 1:10 aqueous dilution with 15%, 20% and 25% cypermethrin. At these dilutions, hazy miniemulsions were obtained that were stable for at least a day at room temperature. At 1:20 dilution of 25% cypermethrin the solution was a clear microemulsion and the particle size was less than 0.04 microns at 90% population. Freeze/thaw stability study between 5 and −10° C. carried out with the microemulsion concentrate containing 15% cypermethrin showed a stable, liquid formulation at the lowest temperature described.

HPLC analysis of the concentrate containing 15% cypermethrin showed greater than 90% retention of a.i. after storing the sample at 52° C. for 18 days.

EXAMPLE 6

The role of N-methylpyrrolidone in the microemulsion of Example 5 was investigated. An inert Matrix M6 was prepared first by mixing 10 g N-octylpyrrolidone, 10 g of Pluronic L31, 60.6 g of Alkamuls EL 620 and 4.3 g of Soprophor 3D-33. A concentrate was prepared by mixing 15 g of cypermethrin with 85 g of Matrix M6. The microemulsion concentrate was diluted at ratios 1:10, 1:100 and 1:1000 with 1000 ppm hard water. All the diluted samples were stable and clear except at 1:100 dilution, where a precipitate was formed. Freeze/thaw stability study between 5 and −10° C. carried out with the microemulsion concentrate showed the sample frozen at −5° C. and lower temperature.

EXAMPLE 7

Similarly, the role of N-octylpyrrolidone in the microemulsion of Example 5 was investigated. An inert Matrix M7 was prepared first by mixing 20 g N-methylpyrrolidone, 8.7 g of Pluronic L31, 52.6 g of Alkamuls EL 620 and 3.7 g of Soprophor 3D-33. A microemulsion concentrate was prepared by mixing 15 g of cypermethrin with 85 g of Matrix M7. The microemulsion concentrate was diluted at ratio 1:10, 1:100 and 1:1000 with 1000 ppm hard water. All the diluted samples were stable and clear except at 1:100 dilution, where a precipitate was formed. Freeze/thaw stability study between 5 and −10° C. carried out with the emulsifiable concentrate showed a stable, liquid formulation at the lowest temperature described.

EXAMPLE 8

Similarly, the role of both N-methylpyrrolidone and N-octylpyrrolidone in the microemulsion of Example 6 was investigated. An inert matrix M8 was prepared first by 11.4 g of Pluronic L31, 68.7 g of Alkamuls EL 620 and 4.9 g of Soprophor 3D-33. A concentrate was prepared by mixing 15 g of cypermethrin with 85 g of matrix M8. The microemulsion concentrate was diluted at ratio 1:10, 1:100 and 1:1000 with 1000 ppm hard water. Precipitate was found in all the diluted samples, except at 1:1000 dilution, where it remained clear. Freeze/thaw stability study between 5 and −10° C. carried out with the microemulsion concentrate showed the sample frozen at 0° C. and lower temperature. Therefore, the results of Example 5 to Example 8 indicate both N-methylpyrrolidone and N-octylpyrrolidone are required to obtain a stable, clear solution with all of the aqueous dilutions in Example 5, and N-methylpyrrolidone is needed to prevent freezing of the samples at temperature below −5° C.

EXAMPLE 9

An inert matrix M9 was prepared first by mixing 19.5 g of N-methylpyrrolidone, 8.6 g N-octylpyrrolidone, 8.6 g of Pluronic L31, 52.8 g of Alkamuls EL 620 and 0.5 g of Rhodafac RA 600. A microemulsion concentrate was prepared by mixing 10 g of cypermethrin with 90 g of matrix M9. The above microemulsion concentrate was diluted at ratio 1:10, 1:100 and 1:1000 with 1000 ppm hard water. The samples diluted at ratio 1:10 and 1:1000 were found clear. The sample diluted at 1:100 ratio was found to precipitate in the form of gel within a day. When distilled water was used in place of 1000 ppm hard water, no gel was found at 1:100 dilution ratio.

EXAMPLE 10

An inert matrix M10 was prepared first by mixing 18.6 g of N-methylpyrrolidone, 8.1 g N-octylpyrrolidone, 8.1 g of Pluronic L31, and 50.2 g of Alkamuls EL 620. A microemulsion concentrate was prepared by mixing 15 g of cypermethrin with 85 g of matrix M10. The above concentrate was diluted at ratio 1:10, 1:100 and 1:1000 with 1000 ppm hard water. All diluted, aqueous samples were found clear.

EXAMPLE 11

An inert matrix M11 was prepared first by mixing 19.7 g of N-methylpyrrolidone, 8.6 g N-octylpyrrolidone, 8.6 g of Pluronic L31, 51.8 g of Alkamuls EL 620 and 1.4 g of Rhodafac RS 710. A microemulsion concentrate was prepared by mixing 10 g of cypermethrin with 90 g of matrix M11. The above concentrate was diluted at ratios 1:10, 1:100 and 1:1000 with 1000 ppm hard water. All diluted, aqueous samples were found clear.

HPLC analysis of the microemulsion concentrate showed greater than 95% retention of a.i. after storing the sample at 52° C. for 18 days.

EXAMPLE 12

An inert matrix M12 was prepared first by mixing 17.5 g of N-methylpyrrolidone, 7.6 g N-octylpyrrolidone, 7.6 g of Pluronic L31, 46 g of Alkamuls EL 620 and 1.2 g of Rhodafac RS 710. A microemulsion concentrate was prepared by mixing 20 g of cypermethrin with 80 g of matrix M12. The above concentrate was diluted at ratio 1:10, 1:20, 1:100 and 1:1000 with 1000 ppm hard water. All diluted aqueous samples were found clear. The particle size at 1:10 and 1:20 dilutions were less than 0.02 and 0.05 microns, at 90% population, respectively.

HPLC analysis of the concentrate showed greater than 95% retention of the a.i. after storing the sample at 52° C. for 18 days.

EXAMPLE 13

An inert matrix M13 was prepared first by mixing 17 g of N-methylpyrrolidone, 7.4 g N-octylpyrrolidone, 7.4 g of Pluronic L31, 22.4 g of Soprophor BSU, 22.5 g of Alkamuls EL 620 and 3.2 g of Soprophor 3D33. A microemulsion concentrate was prepared by mixing 20 g of cypermethrin with 80 g of matrix M13. The concentrate remained stable and single phase after storage in an oven for 13 days at 52° C. The above concentrate was diluted at ratio 1:10, 1:100 and 1:1000 with 1000 ppm hard water. All diluted, aqueous samples were found clear.

EXAMPLE 14

Table 5 shows the microemulsion concentrate for several pyrethroids. An inert matrix M14 was prepared first by mixing 21.9 g of N-methylpyrrolidone, 9.6 g N-octylpyrrolidone, 9.6 g of Pluronic L31, and 59 g of Alkamuls EL 620. Several microemulsion concentrates were prepared by mixing 10 g of either D-allethrin, permethrin, pyperonyl butoxide, or bioresmethrin, with 90 g of matrix M14. Microemulsion concentrates were also prepared with 10 g and 5 g of deltamethrin with 90 g and 95 g of matrix M14, respectively. Microemulsion concentrates were prepared with 15 g and 5 g of penconozole with 85 g and 95 g of matrix M14, respectively. And, microemulsion concentrate was also prepared with 24 g of mixture of D-allethrin/piperonyl butoxide at 4/20 ratio with 76 g of matrix M14. The stability results, at room temperature, of the above microemulsion concentrates after dilution at 1:10, 1:100 and 1:1000 with 1000 ppm hard water are as follows, D-allethrin, permethrin, piperonyl butoxide, and bioresmethrin remained stable and clear upon dilution for 14 days. At 1/10 dilution, 10% deltamethrin precipitated after 3 days, but at 1/100 and 1/1000 dilutions it remained clear for 14 days. However, the dilutions with 5% deltamethrin remained stable and clear for 14 days. At 1/10 and 1/100 dilutions with 15% penconozole a miniemulsion was present, but at 1/1000 it remained a clear microemulsion for 14 days. However, the dilutions with 5% penconozole remained stable and clear for 14 days. Mixture of D-allethrin and piperonyl butoxide at 4:20 ratio was opaque at 1:10 dilution and clear at 1:100 and 1:1000 dilutions.

TABLE 5

| Composition | 1 | 2 | 3 | 4 | 5 | 6 | 7 | 8 | 9 |
|---|---|---|---|---|---|---|---|---|---|
| Microemulsion Concentrate | | | | | | | | | |
| Inert Matrix M14 | 90 | 90 | 90 | 90 | 90 | 95 | 85 | 95 | 76 |
| D-allethrin | 10 | | | | | | | | |
| Permethrin | | 10 | | | | | | | |
| Piperonyl butoxide | | | 10 | | | | | | |
| Bioresmethrin | | | | 10 | | | | | |
| Deltamethrin | | | | | 10 | 5 | | | |
| Penconozole | | | | | | | 15 | 5 | |
| 4/20% D-allethrin/Piperonyl Butoxide | | | | | | | | | 24 |
| | 100 | 100 | 100 | 100 | 100 | 100 | | | 100 |
| Water-Based Microemulsion | | | | | | | | | |
| Properties of Aqueous Microemulsion at Room Temperature observation up to 14 days dilution ratio with 1000 ppm hard water | | | | | | | | | |
| 1:10 | clear | clear | light haze | clear | ppt.* | clear | cloudy | clear | opaque |
| 1:100 | clear | clear | clear | clear | clear | clear | cloudy | clear | clear |
| 1:1000 | clear | clear | clear | clear | clear | clear | clear | clear | clear |

*precipitate on the third day

EXAMPLE 15

An inert Matrix M15 was prepared first by mixing 22 g of N-methylpyrrolidone, 10 g N-octylpyrrolidone, 10 g of Pluronic L31, and 58 g of Alkamuls EL 620. Matrix M15 was added to a premixed agricultural active chemicals (PAA) consisting of 0.05 g allethrin, 0.15 g permethrin, 0.2 g tetramethrin and 1.0 g piperonyl butoxide. The mixture of matrix M15 and PAA were shaken until the agricultural actives dissolved in the inert matrix M15 or the mixture became homogeneous. Normally this took about thirty minutes to two hours. The concentrate obtained was then diluted to 100 grams by adding 1000 ppm hard water following the World Health Organization (WHO) standard and expressed as $CaCO_3$ equivalent. A clear, microemulsion system was found by increasing the amount of the Matrix M15 in the concentrate while maintaining the amount of actives constant, and diluting the concentrate with hard water up to 100 g. The optimal concentration of Matrix M15 in the microemulsion system was found to be 4.01 g in the concentrate. The concentrate and diluted samples were visually examined for clarity, precipitation, and separation or turbidity at ambient temperatures. Stable formulations were observed for 2 weeks. The aqueous microemulsion compositions of the invention made according to the above procedure are summarized from Table 6, wherein the components are in grams.

with 60 g of Igepal CO-630. The concentrate remained stable and single phase on storage. The above emulsifiable concentrate were diluted at ratio 1:10, 1/20, 1:27, 1:40, and 1:100 (5%, 2%, 1.5%, 1% and 0.4% a.i. respectively) with 1000 ppm hard water. All diluted, aqueous samples were found to form two phases within one-half hour after mixing.

TABLE 7

| | Matrix M16 (weight percent) | | |
|---|---|---|---|
| | 70 | 60 | 50 |
| Permethrin | 30 | 40 | 50 |
| | 1:10 dilution with 1000 ppm hard water | | |
| | 3% ai | 4% ai | 5% ai |
| 1/2 hours | haze | cloudy | 2 phases |
| 8 hours | haze | cloudy | 2 phases |
| 1 day | haze | 2 phases | 2 phases |
| | 1:100 dilution with 1000 ppm hard water | | |
| | 0.3% ai | 0.4% ai | 0.5% ai |
| 1/2 hours | clear | cloudy | cloudy |
| 8 hours | clear | cloudy | cloudy |
| 1 day | clear | cloudy | 2 phases |

TABLE 6

| EXAMPLES | 1 | 2 | 3 | 4 | 5 | 6 | 7 | 8 |
|---|---|---|---|---|---|---|---|---|
| Microemulsion Concentrate | | | | | | | | |
| Inert Matrix | 0.00 | 1.00 | 1.99 | 4.01 | 5.99 | 8.01 | 9.00 | 10.60 |
| Premixed Agricultural Actives | 1.4 | 1.4 | 1.4 | 1.4 | 1.4 | 1.4 | 1.4 | 1.4 |
| Water-Based Microemulsion | | | | | | | | |
| 1000 ppm hard water | 98.6 | 97.6 | 96.6 | 94.6 | 92.6 | 90.6 | 89.6 | 88 |
| | 100 | 100 | 100 | 100 | 100 | 100 | 100 | 100 |
| Properties of Aqueous Microemulsion At Room Temperature | | | | | | | | |
| at 0 hr. | 2 phases | milky | hazy | clear | clear | clear | cloudy | cloudy |
| 24 hr. | 2 phases | 2 phases | hazy | clear | clear | clear | clear | clear |
| 2 days | 2 phases | 2 phases | hazy | clear | clear | clear | clear | clear |
| 2 weeks | 2 phases | 2 phases | hazy | clear | clear | clear | clear | clear |

EXAMPLE 16

A series of microemulsion and miniemulsion concentrates were prepared using various amounts of permethrin. An inert matrix M16 was prepared first by mixing 22.2 g of N-methylpyrrolidone, 9.7 g N-octyl-pyrrolidone, 9.7 g of Pluronic L31, and 58.4 g of Alkamuls EL 620. Emulsifiable concentrates were prepared by mixing 30 g, 40 g, 50 g permethrin with 70 g, and 60 g, and 50 g of matrix M16, respectively, as seen in Table 7. The above emulsifiable concentrate were diluted at ratios 1:10, and 1:100 with 1000 ppm hard water. The results of the stability after dilution are shown in Table 7. Further dilutions of the emulsifable concentrates to 1%, 1.5% and 2% permethrin were also undertaken. The stability results are shown in Table 8.

COMPARATIVE EXAMPLES

EXAMPLE 17

An emulsifiable concentrates with permethrin as the active ingredient was prepared by mixing 40 g of permethrin

TABLE 8

| | Matrix M16 (weight percent) | | |
|---|---|---|---|
| | 70 | 60 | 50 |
| Permethrin | 30 | 40 | 50 |
| | Dilution to 1% Permethrin | | |
| | 1% ai | 1% ai | 1% ai |
| 1/2 hours | clear | cloudy | cloudy |
| 3 hours | clear | cloudy | 2 phases |
| 1 day | clear | cloudy | |

TABLE 8-continued

| | Dilution to 1.5% Permethrin | | |
|---|---|---|---|
| | 1.5% ai | 1.5% ai | 1.5% ai |
| 1/2 hours | clear | cloudy | cloudy |
| 2 hours | clear | cloudy | 2 phases |
| 1 day | clear | cloudy | |

| | Dilution to 2% Permethrin | | |
|---|---|---|---|
| | 2% ai | 2% ai | 2% ai |
| 1/2 hours | haze | cloudy | cloudy |
| 2 hours | haze | cloudy | 2 phases |
| 1 day | haze | cloudy | |

While the invention has been described with particular reference to certain embodiments thereof, it will be understood that changes and modifications may be made which are within the skill of the art. Accordingly, it is intended to be bound only by the following claims, in which:

What is claimed is:

1. A microemulsion concentrate for forming an aqueous microemulsion of 0.0005–5 wt. % of a pyrethroid and at least 80 wt. % water, free of nonylphenol ethoxylate, consisting essentially of, in a weight ratio of:

(a) 0.015–4% of N-methylpyrrolidone, (b) 0.005–2% of N-octylpyrrolidone, (c) 0.05–1.5% of an ethoxylated/propoxylated (EO/PO) block copolymer surfactant, (d) 0.04–6% of an ethoxylated castor oil or a tristyryl phenol ethoxylate, and (e) 0.0005–0.6% of a phosphate ester as pH buffer.

* * * * *